(12) United States Patent
Wang et al.

(10) Patent No.: US 7,056,466 B2
(45) Date of Patent: Jun. 6, 2006

(54) METHOD OF MANUFACTURE MEDICAL DEVICES EMPLOYING MICROWAVE ENERGY

(75) Inventors: Lixiao Wang, Maple Grove, MN (US); Jan Weber, Maple Grove, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 109 days.

(21) Appl. No.: 10/212,926

(22) Filed: Aug. 6, 2002

(65) Prior Publication Data

US 2003/0183966 A1    Oct. 2, 2003

Related U.S. Application Data

(63) Continuation-in-part of application No. 10/109,220, filed on Mar. 28, 2002.

(51) Int. Cl.
B29C 35/08    (2006.01)

(52) U.S. Cl. ............... 264/405; 264/40.3; 264/40.6; 264/40.7; 264/454

(58) Field of Classification Search ............ 264/406, 264/408, 412, 454, 457, 479, 489, 40.1, 405, 264/40.3, 40.7; 425/169, 172, 140, 149

See application file for complete search history.

(56) References Cited

U.S. PATENT DOCUMENTS

| | | |
|---|---|---|
| 2,863,174 A | 12/1958 | Schuman et al. |
| 3,620,876 A | 11/1971 | Guglielmo, Sr. et al. |
| 3,874,207 A | 4/1975 | Lemelson |
| 3,957,943 A | 5/1976 | Ogura |
| 3,993,529 A | 11/1976 | Farkas |
| 4,003,554 A | 1/1977 | Chauffoureaux |
| 4,035,547 A | 7/1977 | Heller, Jr. et al. |
| 4,035,598 A | 7/1977 | Van Amsterdam |
| 4,040,162 A | 8/1977 | Isogai et al. |
| 4,093,484 A | 6/1978 | Harrison et al. |
| 4,143,112 A | 3/1979 | Turner |
| 4,298,324 A | 11/1981 | Soulier |
| 4,339,295 A | 7/1982 | Boretos et al. |
| 4,390,482 A | 6/1983 | Feurer |
| 4,407,651 A | 10/1983 | Beck et al. |
| 4,454,234 A | 6/1984 | Czerlinski |

(Continued)

FOREIGN PATENT DOCUMENTS

DE    199 54 960    6/2000

(Continued)

OTHER PUBLICATIONS

International Search Report; PCT US 03/01203, reported dated Jun. 4, 2003.

(Continued)

Primary Examiner—Michael P. Colaianni
Assistant Examiner—Monica A Huson
(74) Attorney, Agent, or Firm—Miller, Matthias & Hull

(57) ABSTRACT

An apparatus and method for molding balloon catheters is disclosed. The balloon may be molded by providing a polymeric tube within a mold having an interior cavity in the shape of the desired balloon. Microwave energy, which may be generated by a gyrotron, may then be directed toward the mold, to heat the polymeric material without heating the mold. Once heated, pressurized fluid may be injected into the tube to blow the polymeric material against the interior cavity whereupon the material can cool to form the balloon or can be further heatset by additional microwave energy and be cooled to form the balloon. In accordance with one embodiment, microwave energy can also be used without a mold to form a medical device.

14 Claims, 6 Drawing Sheets

U.S. PATENT DOCUMENTS

| | | | |
|---|---|---|---|
| 4,483,341 A | | 11/1984 | Witteles |
| 4,512,942 A | * | 4/1985 | Babbin et al. ............... 264/474 |
| 4,568,262 A | | 2/1986 | Feurer |
| 4,671,757 A | | 6/1987 | Volk, Jr. |
| 4,672,972 A | | 6/1987 | Berke |
| 4,760,228 A | | 7/1988 | Kudo |
| 4,764,394 A | | 8/1988 | Conrad |
| 4,859,380 A | | 8/1989 | Ogata |
| 4,860,744 A | | 8/1989 | Johnson et al. |
| 4,930,494 A | | 6/1990 | Takehana et al. |
| 4,950,239 A | | 8/1990 | Gahara et al. |
| 4,977,886 A | | 12/1990 | Takehana et al. |
| 4,989,608 A | | 2/1991 | Ratner |
| 5,104,593 A | * | 4/1992 | Joseph ....................... 264/407 |
| 5,154,179 A | | 10/1992 | Ratner |
| 5,172,551 A | | 12/1992 | Nakajima et al. |
| 5,207,227 A | | 5/1993 | Powers |
| 5,222,543 A | | 6/1993 | Carlstrom et al. |
| 5,290,266 A | | 3/1994 | Rohling et al. |
| 5,296,272 A | | 3/1994 | Matossian et al. |
| 5,324,345 A | | 6/1994 | Rutjes et al. |
| 5,330,742 A | | 7/1994 | Deutsch et al. |
| 5,352,871 A | | 10/1994 | Ross et al. |
| 5,411,730 A | | 5/1995 | Kirpotin et al. |
| 5,421,832 A | | 6/1995 | Lefebvre |
| 5,429,583 A | | 7/1995 | Paulus et al. |
| 5,433,717 A | | 7/1995 | Rubinsky et al. |
| 5,496,311 A | | 3/1996 | Abele et al. |
| 5,514,379 A | | 5/1996 | Weissleder et al. |
| 5,622,665 A | | 4/1997 | Wang |
| 5,628,950 A | | 5/1997 | Schrenk et al. |
| 5,641,423 A | | 6/1997 | Bridges et al. |
| 5,653,778 A | | 8/1997 | Rutjes et al. |
| 5,690,109 A | | 11/1997 | Govind et al. |
| 5,693,376 A | | 12/1997 | Fetherston et al. |
| 5,706,810 A | | 1/1998 | Rubinsky et al. |
| 5,720,939 A | | 2/1998 | Schroder |
| 5,728,079 A | | 3/1998 | Weber et al. |
| 5,744,958 A | | 4/1998 | Werne |
| 5,762,741 A | | 6/1998 | Kodokian |
| 5,762,972 A | | 6/1998 | Byon |
| 5,773,042 A | | 6/1998 | Amano et al. |
| 5,775,338 A | | 7/1998 | Hastings |
| 5,787,959 A | | 8/1998 | Lamanan et al. |
| 5,817,017 A | | 10/1998 | Young et al. |
| 5,844,217 A | | 12/1998 | Hawley et al. |
| 5,855,553 A | | 1/1999 | Tajima et al. |
| 5,908,410 A | | 6/1999 | Weber et al. |
| 5,948,194 A | | 9/1999 | Hill et al. |
| 5,951,513 A | * | 9/1999 | Miraki .................... 604/96.01 |
| 6,004,289 A | | 12/1999 | Saab |
| 6,035,657 A | | 3/2000 | Dobak, III et al. |
| 6,040,019 A | | 3/2000 | Ishida et al. |
| 6,056,844 A | | 5/2000 | Guiles et al. |
| 6,061,587 A | | 5/2000 | Kucharczyk et al. |
| 6,123,920 A | | 9/2000 | Gunther et al. |
| 6,137,093 A | | 10/2000 | Johnson, Jr. |
| 6,176,857 B1 | | 1/2001 | Ashley |
| 6,190,355 B1 | | 2/2001 | Hastings |
| 6,203,777 B1 | | 3/2001 | Schroder |
| 6,207,134 B1 | | 3/2001 | Fahlvik et al. |
| 6,224,536 B1 | | 5/2001 | Pike |
| 6,231,516 B1 | | 5/2001 | Keilman et al. |
| 6,248,196 B1 | | 6/2001 | Waitz et al. |
| 6,270,707 B1 | | 8/2001 | Hori et al. |
| 6,270,711 B1 | | 8/2001 | Gellert et al. |
| 6,272,370 B1 | | 8/2001 | Gillies et al. |
| 6,280,384 B1 | | 8/2001 | Loeffler |
| 6,352,779 B1 | | 3/2002 | Edwards et al. |
| 6,361,759 B1 | | 3/2002 | Frayne et al. |
| 6,368,994 B1 | | 4/2002 | Sklyarevich |
| 6,418,337 B1 | | 7/2002 | Torchia et al. |
| 6,478,911 B1 | | 11/2002 | Wang et al. |
| 6,696,121 B1 | * | 2/2004 | Jung et al. .................. 428/35.7 |
| 2001/0043998 A1 | | 11/2001 | Chen et al. |
| 2001/0054775 A1 | | 12/2001 | Nandu et al. |
| 2002/0095198 A1 | | 7/2002 | Whitebrook et al. |
| 2003/0055449 A1 | | 3/2003 | Lee et al. |

FOREIGN PATENT DOCUMENTS

| | | |
|---|---|---|
| EP | 0 355 423 | 2/1990 |
| EP | 0 525 069 B1 | 3/1996 |
| JP | 2001 314390 | 11/2001 |
| WO | WO 80/02124 | 10/1980 |
| WO | WO 89/11874 | 12/1989 |
| WO | WO 99/033606 | 1/1999 |
| WO | WO 00/64608 | 11/2000 |
| WO | WO 01/51115 | 7/2001 |
| WO | WO 03/035161 | 5/2003 |

OTHER PUBLICATIONS

Pages from Farlow's Scientific Glassblowing Inc.'s website.

U.S. Appl. No. 10/375,719, filed Feb. 25, 2003, Chen.

Ashley, S., assoc. ed., "Electric Plastics," *Mechanical Engineering*, Apr. 1998, http://www.memagzine.org/backisues/apri98/features/plastics/plastics.html (Jul. 3, 2003).

Ballinger, J.R., "MRI Contrast Agents," *MRI Tutor Web Site*, http://www.mriotutor.org/mritutor/contrast.html (Aug. 8, 2002).

Ballinger, J.R. "Introduction to MRI," *MRI Tutor Web Site*, http://www.mritutor.org/mritutor/index.html (Jul. 3, 2003).

Bowman, M., "The Big Chill," http://www.ameslab.gov/News/Inquiry/fall97/bigchill.html (Aug. 8, 2002).

Exploratorium, "Curie Point," http://www.exporatorium.edu/snacks/curie_point.html (Jul. 3, 2003).

Exploratorium, "Curie Temperature," Abstract from http://www.exploratorium.edu/serf/phenomena/curie_temperature.html (Aug. 8, 2002).

Garvin, "What is Physics Good For?", IUPUI, http://webphysics.iupui.edu/251/251Sp97GFApr28.html (Aug. 8, 2002).

Gould, T.A., "How MRI Works, " http://www.howstuffworks.com/mri.htm (Aug. 8, 2002).

Gould, T.A., "How MRI Works," http://electronics.howstuffworks.com/mri.htm/printable (Jul. 3, 2003).

Hesselink, J.R., "Basic Principles Of MR Imaging," http://spinwarp.ucsd.edu/NeuroWeb/Test/br-100.htm (Jul. 3, 2003).

Hornak, J.P., *The Basics Of MRI*, http://www.cis.rif.edu/htbooks/mri/chap-1/chap-1.htm, Chapters 1 and 3 (Jan. 4, 2002).

Hornak, J.P., *The Basics Of MRI*, http://www.cis.rit.edu/htbooks/mri, Chapters 1, 2, 6, 8 and 9 (Jul. 3, 2003).

International Search Report PCT US 03/09494, report mailed Jun. 9, 2003.

King, M.M., "Module #2: Basic Principles Of MRI," http://www.erads.com/mrimod.htm (Aug. 8, 2002).

Koehler, K.R., "Body Temperature Regulation," http://www.rwc.uc.edu/Koehler/biophys/8d.html (Jul. 8, 2003).

Konings, et al., "Heating Around Intravascular Guidewires By Resonating RF Waves," Abstract from *J. Magn. Reson. Imaging*, 12(1):79-85 (2000).

Kuperman, V., *Magnetic Resonance Imaging: Physical Principles And Applications*, Academic Press (2000).

"Laboratory #27: Peltier Elements And Thermistors," Indiana University Dept. of Physics Intermediate Physics Laboratory (P309), http://www.physics.indiana.edu/-dmckinne/p309/ (last modified Nov. 2, 2000).

Ladd, et al., "Reduction Of Resonant RF Heating In Intravascular Catheters Using Coaxial Chokes," Abstract from *Magn. Reson. Med.*, 43(4):615-619 (2000).

Liu, et al., "Safety Of MRI-Guided Endovascular Guidewire Applications," Abstract from *J. Magn. Reson. Imaging*, 12(1):75-78 (2000).

"Magnetism," xrefer, http://www.xrefer.com/entry/489951 (Aug. 8, 2002).

"The Mean Field Model," http://carini.physics.indiana.edu/P616/lecture-notes/mean-field.html (Aug. 8, 2002).

"The Mean Field Model," http://carini.physics.indiana.edu/P616/lecture-notes/mean-field.html (Jul. 3, 2003).

Nitz, et al., "On The Heating Of Linear Conductive Structures As Guide Wires And Catheters In Interventional MRI," Abstract from *J. Magn. Reson. Imaging*, 13(10):105-114 (2001).

"The Nobel Prize In Chemistry 2000," http://www.nobel.se/chemistry/laureates/2000/index.html (Jul. 3, 2003).

"Nobel Prize 2000 For The Discovery And Development Of Conductive Polymers," Panipol Conductive Polymers, Panipol Ltd., http://www.panipol.com/ (Jul. 8, 2003).

"About Technology, Definitions, Advantages, Products, Applications, Evaluation, Techn. History, Contact, References," Panipol Conductive Polymers, Panipol Ltd., http://www.panipol.com/noframes.htm (Ju. 3, 2003).

"The Heatsink Guide: Peltier Coolers," http://www.heatsink-guide.com/peltier.htm (Jul. 3, 2003).

Pierce, J. P., Abstract, Table of Contents, and Chapter 1: "Introduction to Magnetic Nanostructures" in "Tailored Magnetic Nanostructures on Surfaces," available at http://web.utk.edu/~jp/thesisJP.htm, May 2003.

Stephens, J., "Peitier CPU Cooling," http://www.pcmech.com/show/processors/140/ (Aug. 13, 2002).

Tellurex Corporation, "Frequently Asked Questions," http://www.tellurex.com/resource/txfaqc.htm (Sep. 16, 2002).

"'TMD' System Overview," Otari, Inc., http://www.otari.com/products/TMD.html (Aug. 8, 2002).

"Types Of Magnetism," http://www.physics.hull.ac.uk/magnetics/Magnetism/Types/types.html (Aug. 8, 2002).

"Types Of Magnetism," http://www.physics.hull.ac.uk/magnetics/Magnetism/Types/types.html (Jul. 3, 2003).

Wohlgemuth, et al., "Laser-Induced Interstitial Thermotherapy Of The Uterus In An Open MRI System: Preliminary In Vitro And In Vivo Experience," http://www.toshiba-medical.co.jp/tmd/review/rv76/r76_6.thm (Jul. 8, 2003).

International Search Report from PCT/US2004/000848 application; report dated Apr. 6, 2004.

* cited by examiner

METHOD OF MANUFACTURE MEDICAL DEVICES EMPLOYING MICROWAVE ENERGY

CROSS REFERENCE TO RELATED APPLICATION

This application is a continuation-in-part of U.S. patent application Ser. No. 10/109,220 filed on Mar. 28, 2002.

FIELD OF THE DISCLOSURE

The disclosure generally relates to medical devices and, more particularly, relates to methods of manufacturing medical devices.

BACKGROUND OF THE DISCLOSURE

Angioplasty is an effective medical procedure performed to expand constricted sections of blood vessels. In such a procedure, an angioplasty balloon or balloon catheter is navigated to the site of the constriction. The balloon is inflated after reaching the site, by way of fluid pressure injected into the balloon, to thereby expand its dimension. The expansion of the balloon exerts pressure on the vessel walls to thereby widen the vessel and alleviate constriction to blood flow.

Conventionally, such balloons are manufactured from a polymeric material and are molded in a blow molding procedure. More specifically, a cylinder or tube of polymeric material, known as a parison, is placed within a mold having an interior cavity in the desired shape of the balloon. The mold is then heated, with the heat of the mold being conducted to the parison, such that upon introduction of fluid pressure into the parison the polymeric material deforms into the shape of the mold cavity. The mold is then cooled to cause the polymeric material to harden into the shape of the mold.

Typically, the mold is provided in a clam shell design wherein each half of the mold includes half of the interior cavity forming the balloon. The mold can therefore be wrapped around the parison and be easily removed to facilitate production. The parison itself can be heated by immersing the entire mold within a hot water, oil, glycerin, or other fluid bath and allowing the mold and parison to be heated via conduction. One problem associated with such a process is that heating of the parison is less than optimal. Heating via conduction, by its very nature, is a relatively slow process. Moreover, the substantial time it takes to heat the parison in the central section having the widest distance between the mold and the parison, in comparison to the narrow space at both ends, lends itself toward a substantial heat flow axially along the parison at these end sections, which itself tends to heat portions of the polymeric material at which balloon deformation is not desired. Accordingly, such systems typically need to employ some sort of cooling mechanism, such as a cold air jet, to keep the areas of the parison outside of the mold cool. One problem stemming from such a system is that temperature control or distribution across the entire polymeric tube is difficult. For bigger balloon sizes, in which the gap between the polymeric tube and mold wall is too large to give sufficiently fast transfer of heat, small amounts of water are often injected inside the mold between the parison and the mold for better heat conduction. However, it will be clear that this material is obstructing the free expansion of the parison inside the mold.

Moreover, with such conventional systems, it is not possible to heat different axial sections of the polymeric tube to different temperatures. For example, this may be advantageous when it is desired to create different physical properties within the balloon itself such as multiple areas of varying diameter, wall thickness, or multiple areas consisting of different materials to be heated to different temperatures. In a particular example one can think of the following: the tapering of the balloon from the central balloon section towards the shaft causes the wall thickness in the cone to increase towards the shaft section. This material distribution causes the folded balloon to be thicker in these cone sections than within the central section. For reasons of minimizing the profile of the product to achieve better access into the vascular system, one wishes to reduce the amount of material within the cone section and one way would be to heat the cone sections of the balloon to a higher temperature within the molding process in order to thin these sections. This effect of thinning would be the result of the combination of the applied axial force and the lower viscosity of the cone sections compared to the central cooler section. Although a section of the mold can be kept above the fluid bath, and thus have the effect of producing a cooler section in the mold, due to the slow heating process a sharp temperature transition is not possible. It is also not possible to set the metal mold to a different temperature than that to which the polymeric tube is heated. The mold must therefore be cooled down before the balloon can be removed.

In the construction of medical devices in addition to balloons, such as stents, guidewires, vena ceva filters and filter wires, the time required to cure adhesives and polymer coatings and thus facilitate manufacture, is relatively extensive. It would therefore be advantageous if a method could be devised for accelerating the curing process and thus manufacturing time for such medical devices.

SUMMARY OF THE DISCLOSURE

In accordance with one aspect of the disclosure, a method of manufacturing medical devices is disclosed which includes directing microwave energy toward an exposed polymeric tube, forcing pressurized fluid through the tube to deform a section of the tube heated by the microwave energy, detecting movement of the deformed tube, and ceasing direction of the microwave energy and forcing of the pressurized fluid through the tube upon movement of the deformed tube being detected.

In accordance with another aspect of the disclosure, a medical device manufacturing system is disclosed which includes a microwave energy source adapted to impart microwave energy toward a workpiece, a fluid pressure source adapted to direct pressurized fluid through the workpiece, a sensor adapted to monitor a parameter associated with the workpiece, and a controller adapted to receive a signal from the sensor and direct signals to the microwave energy and fluid pressure sources.

In accordance with another aspect of the disclosure, a method of bonding medical device components together is disclosed which includes depositing adhesive between first and second components, engaging the first component against the second component with the adhesive therebetween, and subjecting the first and second components and adhesive to microwave energy.

These and other aspects and features of the disclosure will become more apparent upon reading the following detailed description when taken in conjunction with the accompanying drawings.

Figure 1:
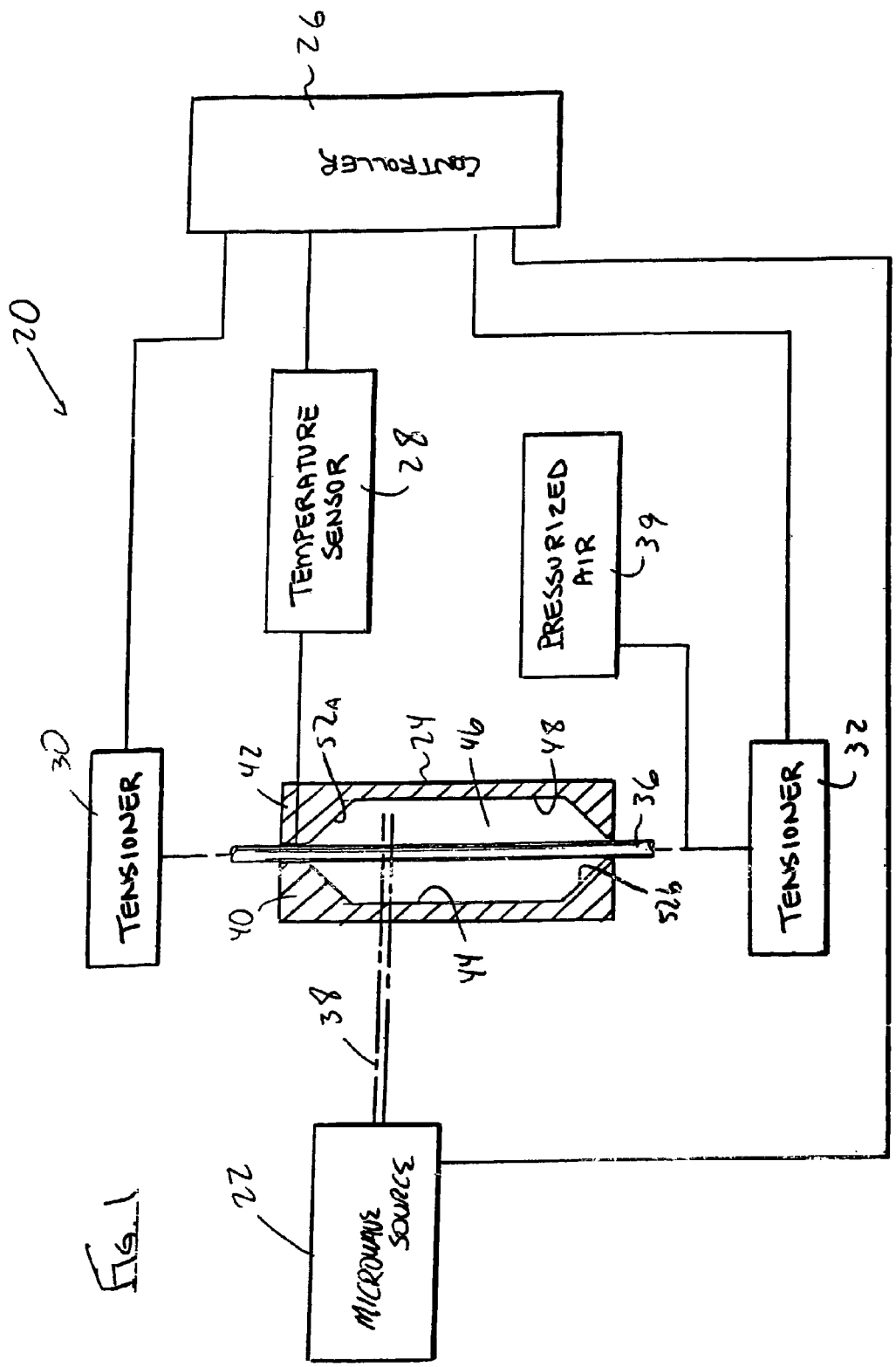
FIG. 1 is a block diagram of a balloon catheter molding apparatus constructed in accordance with the teachings of the disclosure.

While the disclosure is susceptible to various modifications and alternative constructions, certain illustrative embodiments thereof have been shown in the drawings and will be described below in detail. It should be understood, however, that there is no intention to limit the disclosure to the specific examples disclosed, but on the contrary, the intention is to cover all modifications, alternative constructions, and equivalents falling within the spirit and scope of the invention as defined by the appended claims.

DETAILED DESCRIPTION OF THE DISCLOSURE

Referring now to the drawings, and with specific reference to FIG. 1, a balloon catheter molding apparatus, constructed in accordance with the teachings of the disclosure, is generally referred to by reference numeral 20. As described herein, the apparatus 20 may be advantageously employed for the manufacture of balloon catheters and angioplasty balloons, but can be employed in conjunction with many other types of polymeric devices including, but not limited to, other medical devices or components of medical devices, such as contact lenses, graft material, hub mainfolds and the like.

Figure 3:
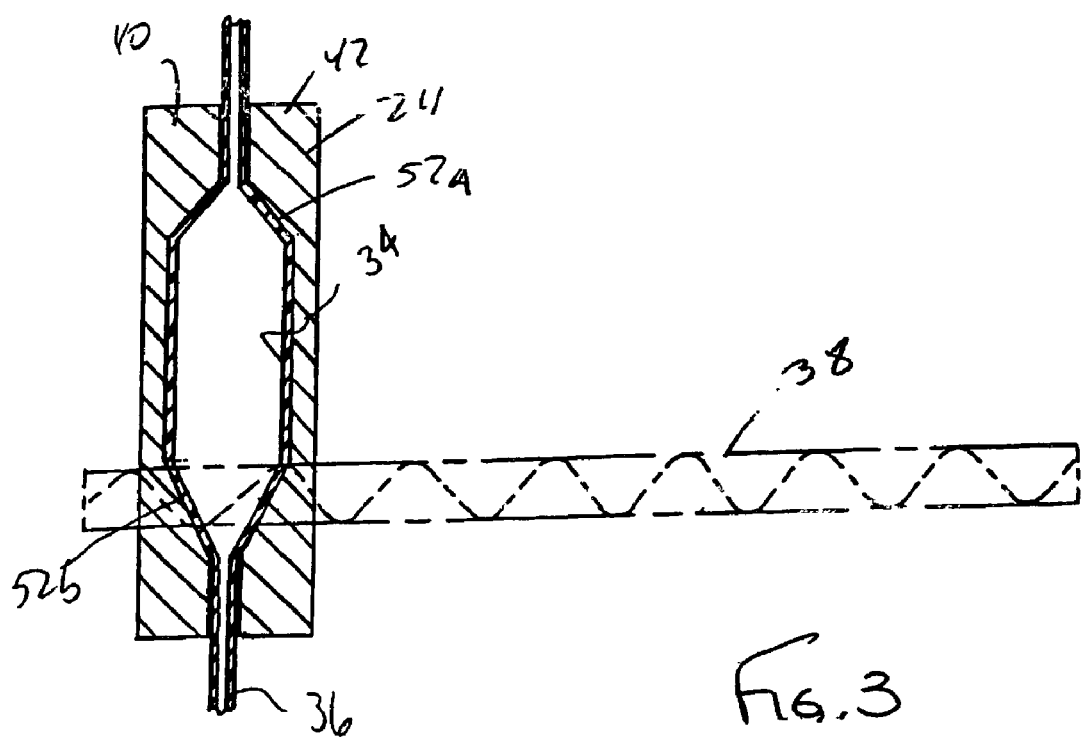
FIG. 3 is a schematic representation of one embodiment of a molding apparatus constructed in accordance with the teachings of the disclosure.

Referring again to FIG. 1, the system 20 may include a source of microwave energy 22, a mold 24, a controller or processor 26, a temperature sensor 28 and first and second tensioners 30, 32. Employing such elements, the apparatus 20 can form a balloon 34 from a workpiece or parison 36. More specifically, the parison 36, which may be provided in the form of a tube or cylinder of polymeric material, is provided within the mold 24. The source of microwave energy 22 then directs a beam or band 38 of microwave energy toward the mold 24, with the microwave energy heating the polymeric material. Prior to heating, during heating, or once heated, pressurized fluid, which may be provided in the form of compressed air from a compressor 39, is injected through the workpiece 36 causing a portion of the workpiece 36 within the mold 24 and heated by the microwave source 22, to expand within the mold 24 as shown best in FIG. 3.

Figure 2:
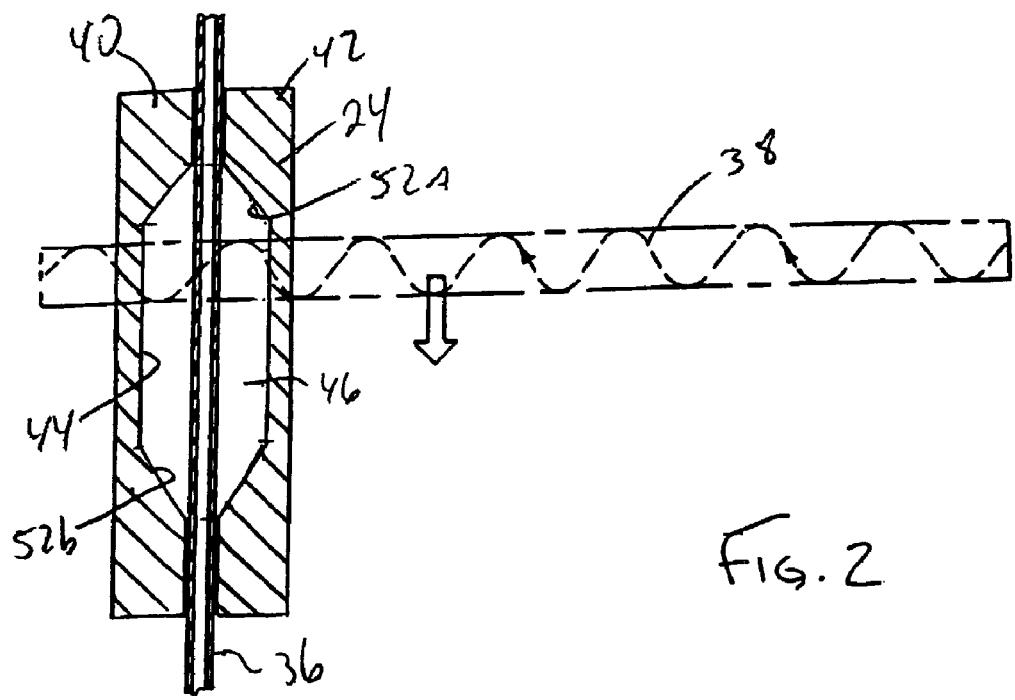
FIG. 2 is a diagrammatic cross-sectional view of a mold and molding process constructed in accordance with the teachings of the disclosure.

Referring now to FIG. 2, the mold 24 is shown in further detail. While it is to be understood that the mold 24 may be provided in a variety of forms, one workable embodiment provides the mold 24 in the form of a clam shell mold having first and second complementary halves 40, 42 with each half 40, 42 having a recess 44 which, when combined, forms the entire mold cavity 46. The cavity 46 is shaped to the desired profile 48 of the balloon 34. In the depicted embodiment, each recess 44 includes a cylindrical outer surface 48 as well as top and bottom canted or conical surfaces 52a, 52b.

Preferably, the mold 24 is manufactured from a microwave-transparent material having a low dielectric loss characteristic, such as a ceramic material or quartz material, although many other types of non-metallic materials, including but not limited to Teflon®, or boron nitride, can be employed with similar efficacy. If the mold 24 is made of Teflon®, for example, or another microwave transparent material that is a poor thermal conductor, application of the microwave beam will allow the temperature of the balloon to be raised to the heatset temperature by applying further microwave energy after the balloon has been blown.

Figure 6:
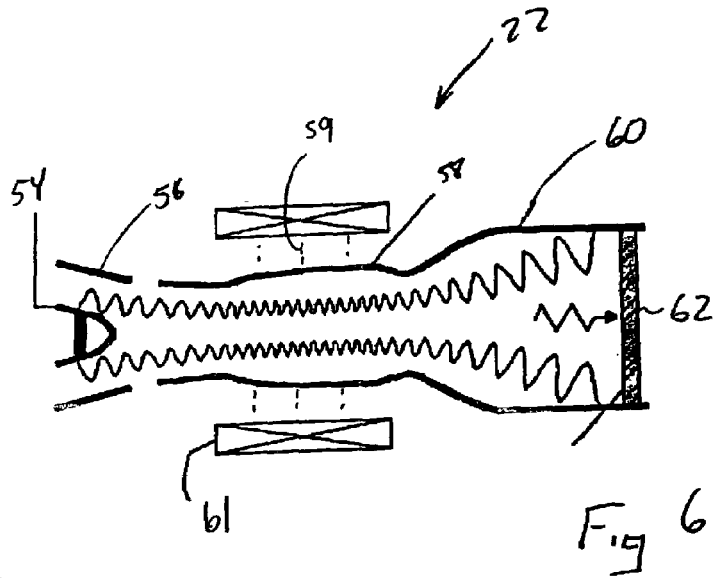
FIG. 6 is a schematic representation of a gyrotron.

With regard to the microwave source 22, it may be provided in the form of a gyrotron adapted to emit microwave energy at a frequency within the range of 2 gigahertz to 110 gigahertz, and a corresponding wavelength within the range of 149.96 mm to 2.72 mm. A common frequency of such gyrotrons is 2.45 gigahertz, with an advantageous range being 20–100 gigahertz. As shown in FIG. 6, the gyrotron may consist of an electron gun having a cathode 54, an anode 56, a resonance chamber 58 immersed in a strong magnetic field 59, and a collector 60. The magnetic field 59 may be generated by superconducting magnets or solenoids 61. When the cathode 54 is energized, accelerating electrons emitted thereby enter the magnetic field 59 and start to spiral, or gyrate, at a high relativistic speed and in very small loops. An advantage of using microwave energy as opposed to, for example, infrared, is the tremendous speed of heating.

For example, using a magnetron injection-type electron gun with the cathode 54 potential at ten kilovolts and a magnetic field 59 of twelve Tesla will result in the electrons being gyrated in a spiral with a radius of 30 micrometers and a cyclotron frequency of 330 GHz. Changing the magnetic field 59 enables the frequency to be changed accordingly. In order to obtain a high frequency wave, the resonant cavity should be designed in such a way that its geometric size matches a harmonic of the wavelengths created by the gyrating electrons. The electromagnetics transmitted through the radio frequency (RF) window 62, and by means of a waveguide 63, can be transported to the target. Manufacturers of gyrotron systems deliver such gyrotrons with built-in mode converters to convert the beam to a gaussian-shaped He11 mode, which can be guided through a circular wave guide with low loss. For example, Insight Product Company of Brighton, Mass. provides such a system. The He11 mode radiated from an open-ended circular waveguide has an axisymmetric narrow Gaussian beam with well-defined polarization and direction, and low-side lobe level enabling the use of simple optical components like metal mirrors and HDPe lenses to focus the beam on a target.

With regard to the power level required to heat the workpiece 36, if the parison is manufactured of Pebax®, in order to bring the workpiece 36 from room temperature to 140° Celsius, and be able to blow a balloon, the required energy can be calculated according to the following. By way of example only, a typical parison tube can be, for example, 1 mm in an outer diameter, and 0.6 mm in the inner diameter, and have a length of 32 mm. The volume of such a tube therefore is 12.8 cubic mm. Taking a CP value of 1500 Joules per kilogram degree Celsius and a density of 1.1 grams/cm$^3$, this means that 2.54 Joules are required to heat the parison from room temperature to 140° Celsius. A commercial low power gyrotron, for example, that manufactured by Insight Product Co., which offers a 24 GHz continuous wave gyrotron with the output power being continuously regulated in the range of 0.1–3 kW by varying the electron beam voltage, up to a maximum of 12 kV, can be defocused roughly to its wavelength, i. e., 12 mm. Therefore when the parison is placed in the focus of the beam about 1/12 of the beam will hit the target. Assuming a 50% absorption of the energy, this means that at 0.1 kW CW output power, it will take about 2.54 Joules/(100(Joules))/24)=0.6 seconds to heat the parison.

Referring again to FIG. 1, not only can the apparatus 20 be used to manufacture balloons using microwave energy, but through the use of the temperature sensor 28 and the processor 26, a feedback loop is provided to thus enable the gyrotron 22 to be modulated based on the heated temperature of the workpiece 36. A suitable temperature sensor would be a model number OS 1592 Fast Response Infrared Fiber Optic Thermometer available through Newport Corporation, which gives about forty readings per second, or an infrared temperature sensor from Heitronics Corporation.

To control the power output of the gyrotron the pulse links of the input voltage on the cathode 54 could be adjusted. By doing so, it would be possible to, for example, operate a 10 kilowatt gyrotron at an average power level of 5 watts or even lower. If the end temperature should be controlled within plus or minus 2° C. (3.6° F.), the rise of the temperature should be less than 2° C. (3.6° F.) for every pulse in between the sensor readings. Therefore, there should be at least 60 readings in between 20° and 140° Celsius assuming a constant absorption coefficient of the polymer material as a function of the temperature. The update frequency of the Heitronics IR sensor is 200 Hz. Taking the earlier calculated 0.6 seconds to rise the parison 120° Celsius into account, which is 200° Celsius per second, and assuming for the time being a simplistic model of a linear rise, reading the IR sensor at 200 Hz will result in an accuracy of 1° Celsius. This demonstrates that it is not unrealistic with existing equipment and sensors to realize a control temperature rise in the parison to 140° Celsius with a precision of ±2° C. within less than 2 seconds.

In an alternative embodiment, the gyrotron beam could be defocused so that only a small percentage of the beam impinges upon the sample. For example, this could be done using a cylindrical lens. In so doing, a much smaller temperature rise could be achieved and the gyrotron could be stopped once the required temperature is reached. Similarly, the current of the cathode could be reduced thereby reducing the output power of the gyrotron. In a still further embodiment, use of a power splitter such as a polarizing splitter could be used to enable a 50/50 power split. Three of these such splitters in series would enable the power level to be reduced to 12.5%. One could also use the 50/50 splitting operation to do multiple balloon blowing at the same time. Defocusing the laser beam would also allow to heat multiple parisons at the same time. Excess energy could be redirected and absorbed by a water load.

Figure 4:
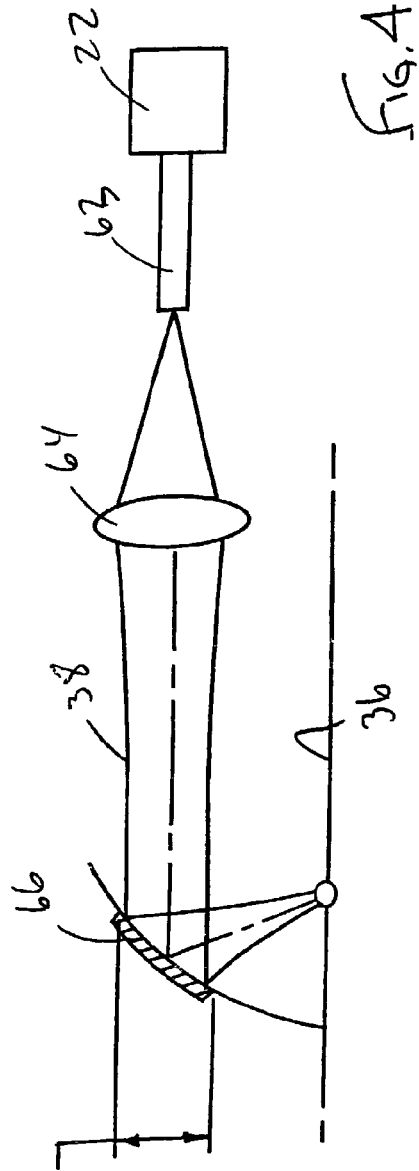
FIG. 4 is a diagrammatic representation of another alternative embodiment of a molding apparatus constructed in accordance with the teachings of the disclosure.
Figure 5:
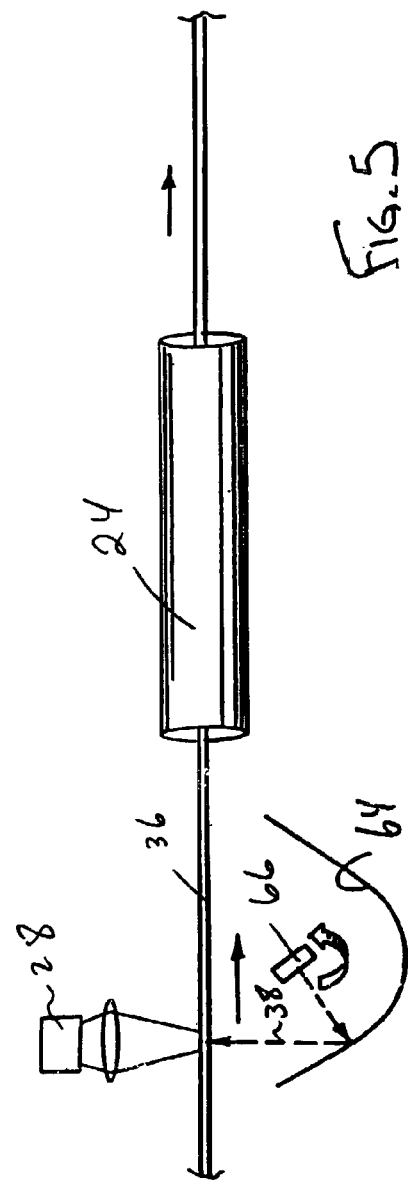
FIG. 5 is a diagrammatic representation of another embodiment of a molding apparatus constructed in accordance with the teachings of the disclosure.

In order to focus the microwave output upon the workpiece 36 and provide an even heating profile across the balloon 34, the embodiments depicted in FIGS. 4 and 5 may be employed. In both embodiments, lenses are employed to focus the beam. For example, as shown in FIG. 4, the microwave source, which may be provided in the form of a gyrotron 22, directs microwave radiation through a waveguide 63 to a first lens 64, which in turn directs the focused microwave beam to a second lens 66. The first lens may be provided as an HDPE lens, while the second lens 66 may be an accurate or focusing metallic mirror. Such lenses are readily, commercially available, such as through Farran Technology. One way of fabricating the balloon is to put the output of the circular wave guide 62 in the focal point of the HDPE lens in order to create a parallel beam and to direct that beam into a focusing mirror as shown in FIG. 4. Such operation will give a slightly inhomogeneous power distribution over the length of the polymer tube.

Alternatively, the beam could be scanned along a part of the tube to achieve a more uniform temperature distribution. This can be done by focusing the beam on a mirror which makes an angle, e.g., 45°, with the optical axis and which rotates around that optical axis as shown in FIG. 5. The beam is thereby scanned in a plane perpendicular with the optical axis. By putting the scanning mirror in the focal point of the parabolic mirror, a system is created wherein the beam can be scanned in one direction along the parison. This also allows a convenient way in which to integrate the infrared sensor. The microwave is focused by the scanning mirror and the focusing lens on a small part of the parison, e.g., on the order or the wavelength. The IR detector's position is perpendicular and is focused to the starting point of the scanned length on the parison.

As shown in FIG. 5 therein, a second lens 66 is a rotating lens which thus enables the focal point of the microwave energy to be not only focused, but moved across the axial length of the balloon 34. Moreover, the first lens 64 is provided in the form of a parabolic lens or mirror. The microwave beam is focused by the scanning mirror and the focusing lens on the small part of the parison. The infrared detector is positioned in a perpendicular direction and is focused to the starting point of the scan length on the parison. While the beam scans across the parison, the infrared sensor monitors the parison. As every point along the parison is receiving the same energy, all points will go to the same heated temperature. Once heated to the correct temperature, the parison is drawn quickly into the mold and the balloon can be blown. In another embodiment one could close a clamshell mold once the parison has reached its temperature. This would avoid having to move the parison. In the case of a pulse microwave system, a much higher pulse frequency is chosen achieving a significant overlap between two adjacent spots. In the case of a CW gyrotron even distribution is automatically obtained. It should be understood that there will be a drop in temperature while the parison is being transported into the mold, or during the closing of the mold, after the heating operation. This can be compensated for by monitoring the rate of this drop and, as the time of transportation is known, compensate for the drop in the heating cycle. This also allows a temperature profile to be achieved along the parison. For example, if it is desired to heat a certain section of the parison to a higher temperature, the infrared sensor can be focused at the high temperature and once the lowest temperature of the profile is reached, those pulses passing over the low temperature sections can be stopped.

Figure 7:
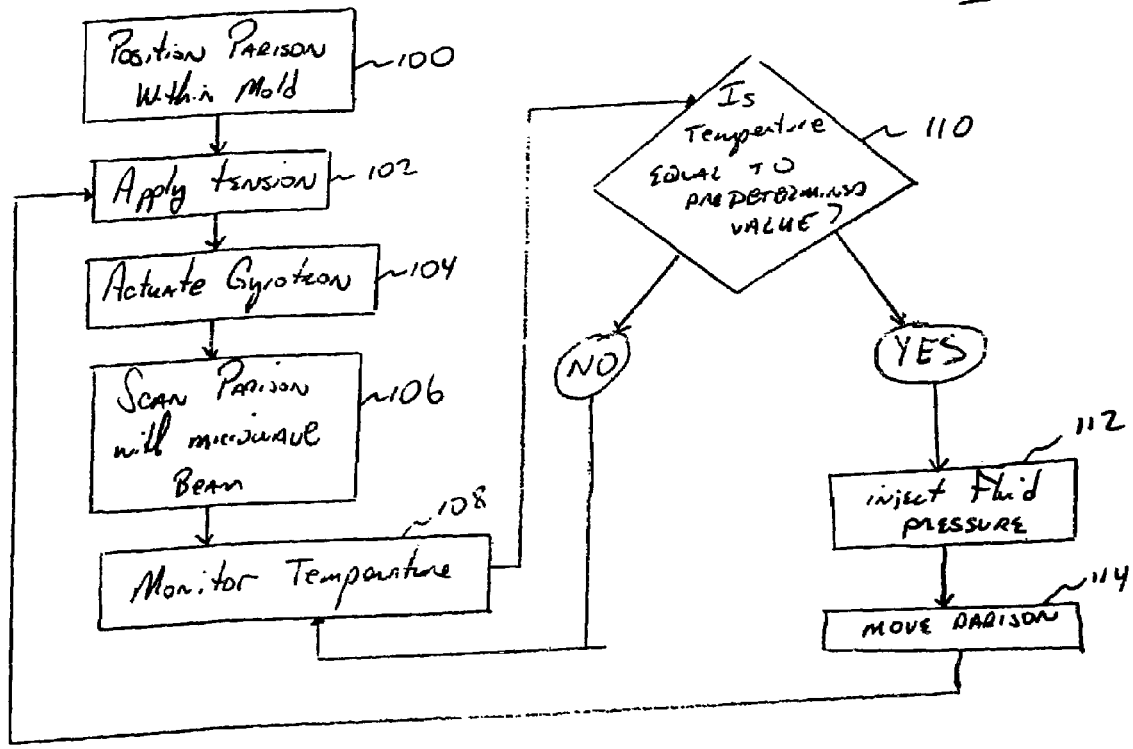
FIG. 7 is a flowchart depicting a sample sequence of steps which may be taken accordingly to the method disclosed herein.

Turning now to FIG. 7, a flowchart depicting a sample sequence of steps which may be taken according to the method of the disclosure is provided. As shown therein, a first step would be to position the parison workpiece 36 within the mold, as indicated by a step 100. Thereafter, if desired, the tensioners 30 and 32 may be actuated if desired to place the parison under tension during the heating process aided by step 102. The tensioners 30, 32 may be provided in a variety of readily available forms including, but not limited to, hydraulic or pneumatic clamps, rotating mandrels or spools, or the like. Once under tension, the gyrotron can be actuated, as indicated in step 104, with the microwave beam generated thereon being scanned across the parison as indicated by step 106. During such scanning, the temperature of the parison is continually monitored by the temperature sensor 28 as indicated in step 108. If the monitored temperature is equal to a predetermined level or within a predetermined range as is determined by the controller 26, as indicated in step 110, the compressor 39 can be actuated to direct pressurized air through the parison as indicated in step 112. Alternatively, the controller 26 may employ an algorithm wherein the gyrotron 22 is modulated in intensity based on the temperature readings. Thereafter, the parison can be moved through the mold 24 as indicated in step 114 and positioned to restart the process. Alternatively, if the monitored temperature is not within such a predetermined range, the temperature continues to be monitored until reaching such level.

Figure 8:
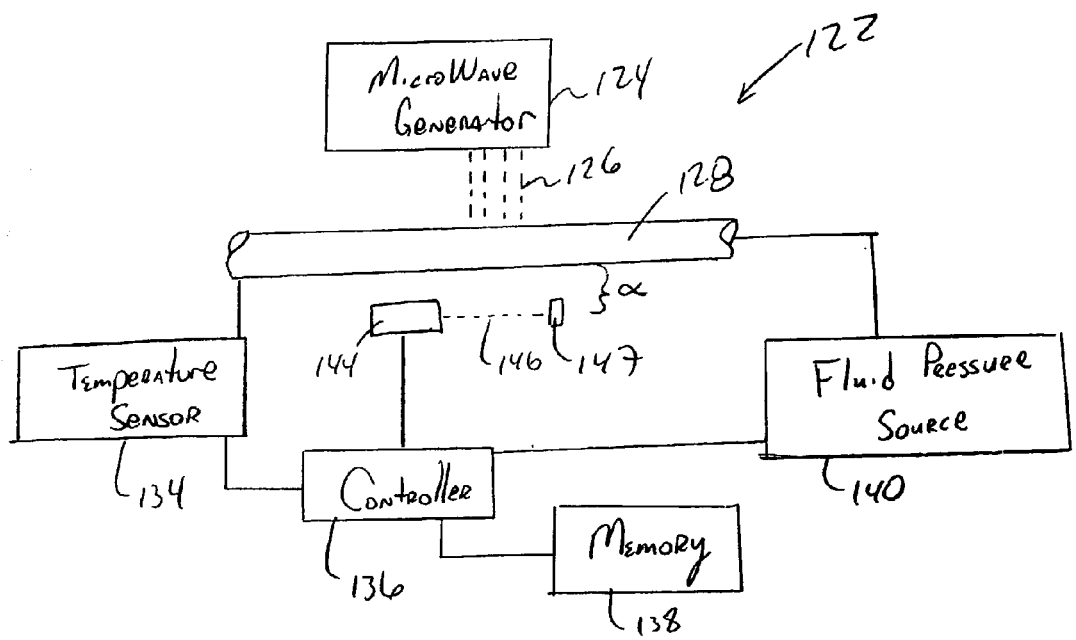
FIG. 8 is a schematic representation of a medical device manufacturing system constructed in accordance with the teachings of the disclosure, with the medical device being heated.
Figure 9:
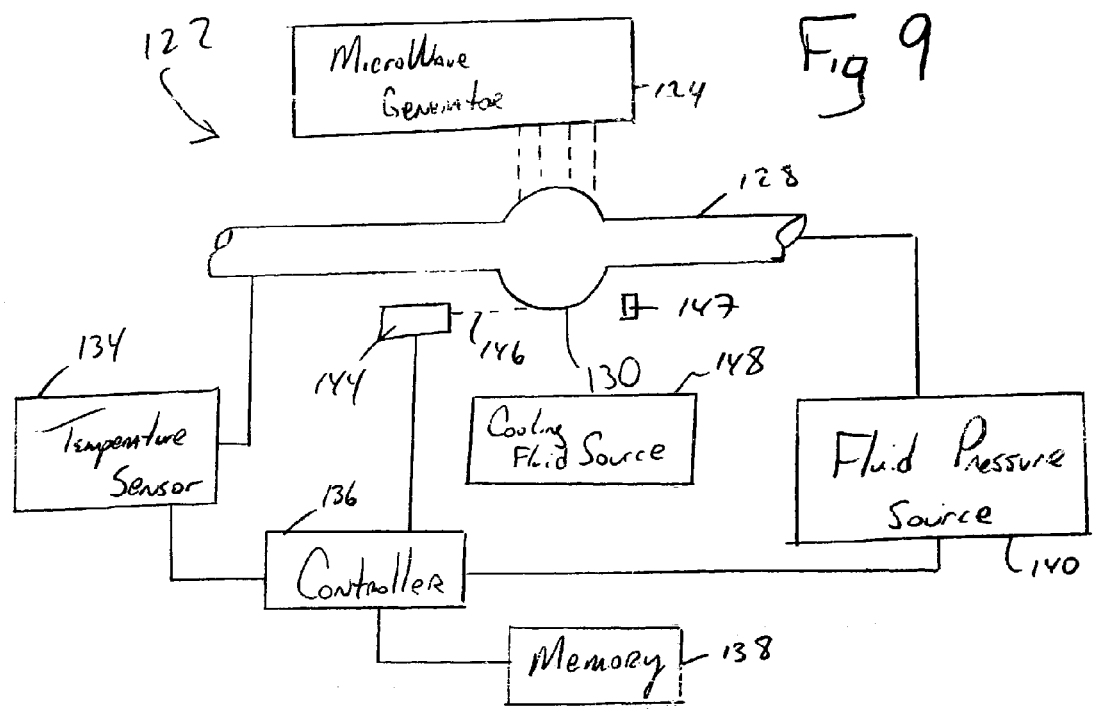
FIG. 9 is a schematic representation similar to FIG. 8, but with the medical device being pressurized and expanded.

In a still further embodiment illustrated in FIGS. 8 and 9, a medical device could be constructed without using a mold of any kind. In such a system, referred to herein as free blowing, manufacturing could be facilitated and accelerated in that the additional labor required for adding and removing the mold or removing the workpiece from the mold can be eliminated. More specifically, as depicted in the figures, a system 122 could be provided similar to the above-referenced embodiments in many ways but not including the mold. A gyrotron 124 or other source or microwave energy is provided to direct a beam of energy 126 toward a workpiece or parison 128 as indicated above. The beam 126 can be scanned back and forth over the entire parison 128, or directed to a specific location such as the desired location for a balloon 130 (FIG. 9) forming part of a balloon catheter, or the like.

An added benefit of manufacturing a medical device 20 without a mold is the free access to the parison 128 it affords, thereby facilitating rapid and complete temperature detection. As indicated in the figures, a temperature sensor 134, (or temperature sensors) could be provided so as to take accurate and frequent temperature sensor readings and in turn direct a temperature signal to a controller 136. The controller 136, which could be any form of microprocessor based computing device, or even just an analogue electronic system, can compare the read temperature of the parison 128 and, upon reaching a threshold temperature stored in a memory 138, dispatch a signal to a fluid pressure source 140 to direct a stream of pressurized fluid into the parison 128 as indicated in FIG. 9.

Since the gyrotron is an electron beam, the energy of the gyrotron beam 126 can be modulated exactly and quickly. In other words, while sweeping the beam 126 over the parison 128, the start and stop positions for the beam, as well as the energy distribution along the swept path, can be precisely controlled. This can be at a single energy level to heat the parison 128 to the same temperature between start and stop positions, or a temperature distribution along the parison can be generated by modulating the energy while sweeping. Since the temperature absorption rate of the workpiece is a non-linear function of the temperature of the workpiece, in order to be able to bring the workpiece to any predefined temperature, a feedback loop provided by the temperature sensor 134 and the controller 136 is advantageous. For example, an infrared radiation pyrometer such as model number KT22 manufactured by Heitronics Corporation is useful in that it has a response time of less than five milliseconds to an accuracy of 0.1° Kelvin. The temperature sensor manufactured by Impac under its model number Infratherm YP10 is also useable in that it has a response time of two milliseconds. Moreover, both sensors can focus down to spot sizes smaller than 0.5 millimeter, which is smaller then the diameter of most parisons.

Using such a feedback loop, while sweeping the product multiple times with an electron beam, one can monitor the temperature of the product at a single point and stop the heating process when the predefined temperature has been achieved. In such a way, any temperature within the range of, for example, room temperature to 400° C., can be achieved within less than a second. Using the KT22 pyrometer sensor it is possible to measure only at a single point, but there are also infrared line scanners, which can sense the temperature along the complete product. If the entire tube is scanned with the microwave beam using the same energy level, then sensing a temperature at a single point along the tube will be sufficient to obtain a good measure of temperature along the entire product. Even when a temperature profile is created along the tube by changing the energy of the microwave beam as a function of the position along the tube, measuring the temperature at a single point which receives the highest energy is sufficient to tell the temperature along the entire line.

Referring now specifically to FIG. 9, it can be seen that upon introduction of fluid pressure into the workpiece 128 by the fluid pressure source 140, the heated section (balloon 130) of the parison 128 is expanded. This is because the heat generated by the gyrotron is sufficient to heat and weaken the parison 128 at the desired location for the balloon to a greater degree than the remainder of the parison 128. Accordingly, the force generated by the fluid pressure is able to deform the heated, weakened section of the parison 128, while leaving the remainder unchanged.

In order to accurately form the balloon 130, without the use of a mold, at least one position sensor 144 can be provided. For example, as indicated in FIG. 9, an optical scanner such as a laser scanner can be positioned so as to direct a laser beam 146 across to a receiver 147 at a distance α from the parison 128 corresponding to the desired dimension for the balloon 130. Upon the balloon 130 reaching such dimension, the beam 146 is broken whereupon the position sensor 144 then directs a signal to the controller 136 indicating same. Upon receipt of such a signal, the controller 136 then directs the fluid pressure source 140, or a valve associated therewith, to reduce the pressure of the fluid inside the parison 128 and stop further expansion. Another embodiment would use a focused microwave to heat a small portion of the parison and upon expansion of that section, signaled to the processor by the signal of the distance sensor, the processor would force to either move the parison in axial direction or move the microwave beam. In other words, the balloon blowing process would be a continuous process along the axial direction instead of a simultaneous process. By repeating these processing steps over the same balloon section, one could expand the balloon in gradual steps.

Moreover, a cooling source 148 can be provided to facilitate curing of the parison 128 upon the balloon reaching its desired dimension. For example, low temperature nitrogen gas, air, helium gas, or the like can be blown against the balloon 130 when cooling is desired. Such cooling gas, in conjunction with the cessation of microwave energy and fluid pressure, will facilitate immediate setting of the polymer material. In addition to Pebax® and the other materials indicated above, the system 122 can be used in conjunction with various other types of materials, including, but not limited to, polyimide, polyimide 12 PEEK (polyetheretherketone), PTFE (polytetrafluoroethylene) and PET (polyethylenterephthalate), polyetherpoly(2,6-dimethly1-phenyleneether), polyetherketone, blends of such materials, or any other high or low temperature polymer.

The parison 128 can also be extruded or otherwise manufactured from two or more polymers with an objective to create balloons with a greater variety of mechanical performance in different sections of the balloon. A typical example would be to create a balloon with a non-compliant central section and a compliant end section in order to produce a 'dog-bone' type of balloon, enabling the injection of a drug in the enclosed space between the central section of the balloon and the arterial vessel wall. The compliant end sections would allow for a seal with the vessel wall, whereas the non-compliant central section would allow for annular space between the balloon and the vessel wall. If the second polymer has a different glass transition temperature than the first polymer, as well as a different mechanical strength, both polymers have to be heated to different temperatures, in order for both polymers to be amenable to balloon formation upon injection of fluid pressure. In other words, using the ability of the microwave heating process to heat different sections of the parison to different temperatures, one is enabling such balloon designs combining two or more polymers. Although, not limited to such a temperature it has been found by the inventor that some high strength polymers such as polyimide with a glass transition point of at least 215° C. are advantageous in the creation of high strength thin walled balloons The required high balloon blow-molding temperatures make it impossible to process these materials using the conventional balloon blow process due to the axial flow of energy. The speed of microwave heating offers the ability to free-blow balloons with a temperature gradient along the parison of at least 25° C. per millimeter inside the mold. As this cannot be done by other means due to the axial flow of energy, it offers more materials to be used along the axial line of the parison. As explained before, the speed of heating also enables a balloon to be blown in less than two seconds at temperatures higher than 140° C. offering the advantage of reduced thermal degradation of the polymer during the balloon blow process.

Figure 10:
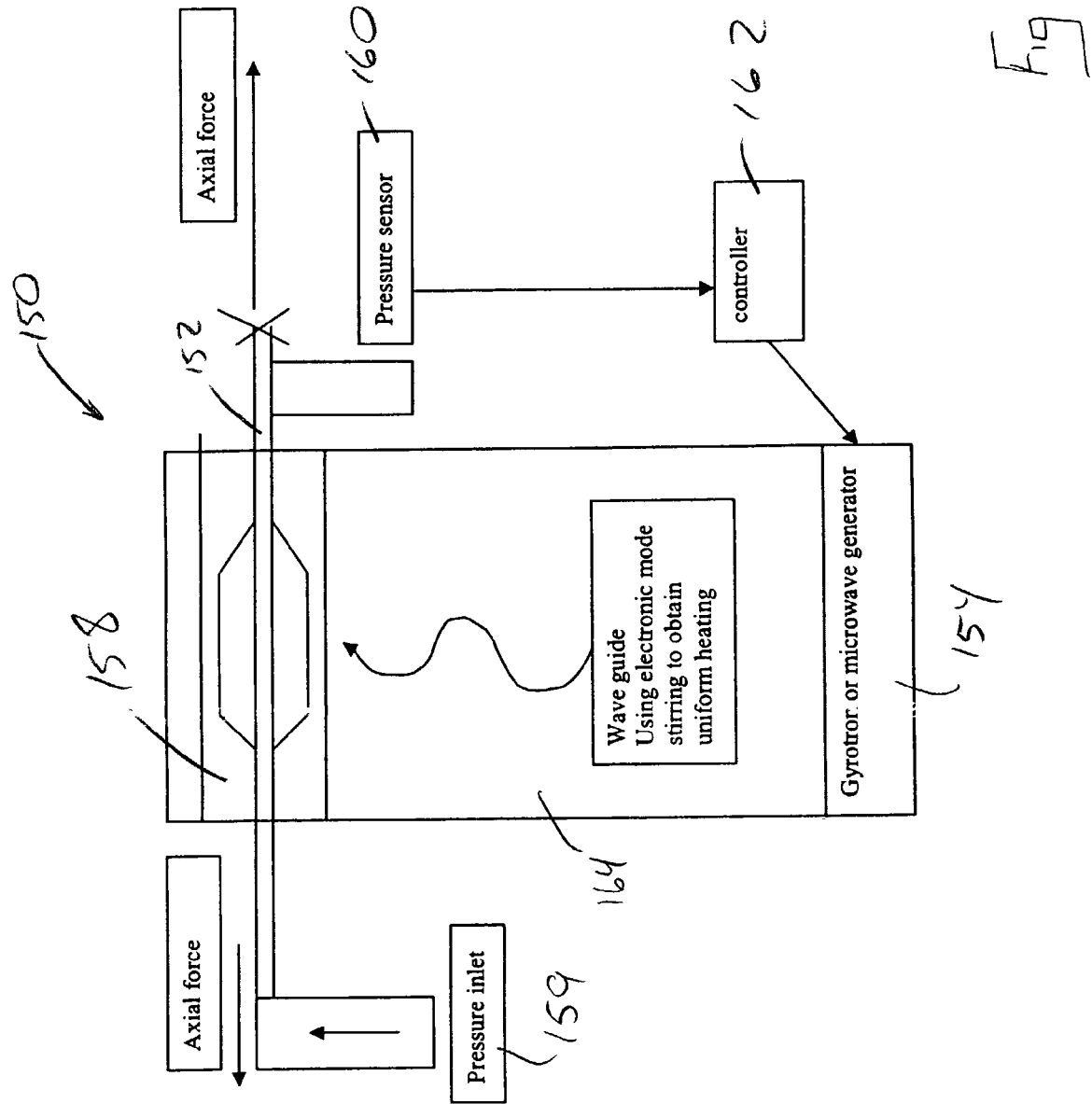
FIG. 10 is a schematic representation of a medical device manufacturing system employing a pressure sensor.

In a still further system 150 depicted in FIG. 10, fluid pressure is directed through a parison 152 prior to and/or during heating of the parison 152 by gyrotron 154. Accordingly, once the parison 152 reaches a threshold temperature at which the material of the parison becomes too weak to sustain its shape, it will expand, forming a balloon. Such an embodiment could be used with or without a mold 158, with fluid pressure being directed through the parison 152 via a fluid pressure source 159.

In such an embodiment, the drop in fluid pressure within the parison 152, resulting from the expansion of the parison 152, can be used as an indirect temperature control to deactivate the gyrotron 154, and thus cease heating of the parison 152. More specifically, as indicated in FIG. 10, a pressure sensor 160 could be provided to constantly monitor the fluid pressure within the parison 152. The pressure sensor 160 in turn sends a corresponding signal to a controller 162. Once the parison 152 reaches a temperature at which the fluid pressure is sufficient to deform the parison 152 and form the balloon, the pressure within the parison 152 will drop due to the expansion of volume. The resulting drop in pressure will be transmitted via a corresponding signal from the pressure sensor 160 to the controller 162, with the controller 162 in turn directing a signal for deactivating the gyrotron or other microwave source 154. As the heating is done very quickly, very responsive pressure sensors are desirable, such as a Kistler model No. 601A or 701A.

As indicated above, microwave energy can be generated by a gyrotron used in conjunction with a plurality of fixed and/or moveable lenses to create a quasi-optical system. However, in an alternative embodiment, one could also place the workpiece within a waveguide. However, since only certain wave modes fit within a certain guide geometry, only certain wave modes are directed to the workpiece giving in essence a very non-uniform heating. Therefore, in order to achieve uniform heating, one could apply either mechanical or electrical mode stirring. In mechanical mode stirring, such as used in a variety of conventional microwave heaters, one changes continuously the geometry of the waveguide in order to change the preferred wave mode. In electronical mode stirring (variable frequency) one sweeps repeatedly and continuously through a frequency band or domain causing the same mode-stirring effect. To achieve a very uniform heating result within this almost instantaneously heating process, it is clear that the mode-stirring frequency has to be very high and the stirring has to run through a large spectrum of wavemodes and by that one could say that an electronic mode-stirring is by definition more applicable.

In the embodiments specifically mentioned above, a balloon catheter is being manufactured. However, it is to be understood that microwave heating can be used in manufacturing various other medical devices or components including, but not limited to, connecting a manifold to a catheter shaft using adhesive, connecting layers of a medical device together using a microwave absorbent material such as a carbon in between the layers or curing a polymer coating or the like to the outer surface of a stent, filter wire, or other polymer metal or ceramic device. Under conventional systems, the adhesive is simply allowed to cure under room temperature, often resulting in relatively long manufacturing cycles, or displacement of the adhesive turning the process. However, by directing microwave energy toward such adhesives, curing time are greatly reduced. The process can be further accelerated by including electrically conductive fibers in the adhesives. A very suitable electric conductor is carbon, which comes in a variety of shapes and powder sizes, on the order of microns and nano-sized fibers.

In order to enable such microwave energy to be used in curing a polymer coating onto a metal substructure, a variable frequency microwave applicator can be employed. Microwaves are often not used in conjunction with metal objects in that sparking or arcing results from excessive charge buildup in the metallic material in the presence of standing wave patterns. However, with a variable frequency microwave technique, the electric fields generated are electronically stirred and the microwave energy is not focused on any given location for more the a fraction of a second. The dynamics of charge buildup that lead to sparking are therefore never achieved, hence leading to no arcing. As such, this enables the positioning of stents, filter wires, vena ceva filters, or any other metal structure inside a variable frequency microwave applicator.

Based on the foregoing, one of ordinary skill in the art will readily understand that the teachings of this disclosure can be employed to create a system for effectively and quickly molding medical devices.

What is claimed is:

1. A method of manufacturing medical devices without a mold, comprising:
    directing microwave energy toward an exposed polymeric tube, no mold being provided around the polymeric tube when the microwave energy is directed toward the polymeric tube; and
    forcing pressurized fluid through the tube to deform a section of the tube heated by the microwave energy;
    detecting movement of the deformed tube to a predetermined distance; and
    ceasing direction of the microwave energy and forcing of the pressurized fluid through the tube upon movement of the deformed tube to a predetermined distance being detected.

2. The method of claim 1, wherein the directing step is performed by a gyrotron.

3. The method of claim 1, wherein the microwave energy is generated in a repeating pattern within a frequency domain.

4. The method of claim 1, wherein the detecting step is performed by an electronic position sensor.

5. The method of claim 3, wherein the ceasing step is performed by an electronic control after receiving a signal from the position sensor.

6. The method of claim 4, wherein the position sensor is an optical sensor.

7. The method of claim 1, wherein the forcing step is performed during the directing step.

8. The method of claim 7, further including the step of detecting pressure within the tube and performing the ceasing step where a drop in pressure is detected.

9. The method of claim 1, further including the step of sensing the temperature of the tube during the directing step and initiating the forcing step when the sensed temperature reaches a predetermined level.

10. The method of claim 1, where the medical device is a balloon component of a balloon catheter.

11. The method of claim 10, wherein the balloon catheter is manufactured from a material selected from Polyamide 12, Polyimide, Pebax, polyethylene terephthalate, polytetrafluoroethylene, polyetheretherketone, and blends using one or more, of these materials.

12. The method of claim 1, wherein the cooling fluid is selected from the group consisting of nitrogen gas, air, and helium gas.

13. A method of manufacturing medical devices, comprising:
    directing microwave energy towards an exposed polymeric tube;
    forcing pressurized fluid through the tube to deform a section of the tube heated by the microwave energy, the forcing step expanding the tube in less than two seconds after the directing step heats the balloon to at least 100° C.;
    detecting movement of the deformed tube to a predetermined distance; and
    ceasing direction of the microwave energy and forcing of the pressurized fluid through the tube upon movement of the deformed tube to a predetermined distance being detected.

14. A method of manufacturing medical devices, comprising:
    directing microwave energy toward an exposed polymeric tube;
    forcing pressurized fluid through the tube to deform a section of the tube heated by the microwave energy, the forcing step expanding the tube in less than two seconds;
    detecting movement of the deformed tube to a predetermined distance; and
    ceasing direction of the microwave energy and forcing the pressurized fluid through the tube upon movement of the deformed tube to a predetermined distance being detected.

* * * * *

UNITED STATES PATENT AND TRADEMARK OFFICE
CERTIFICATE OF CORRECTION

| | | |
|---|---|---|
| PATENT NO. | : 7,056,466 B2 | Page 1 of 1 |
| APPLICATION NO. | : 10/212926 | |
| DATED | : June 6, 2006 | |
| INVENTOR(S) | : Wang et al. | |

It is certified that error appears in the above-identified patent and that said Letters Patent is hereby corrected as shown below:

On page 2, under Other Publications:

Ballinger, J.R., "MRI Contrast agents," MRI Tutor Web Site, http://www.mriotutor.org/mritutor/contrast.html (Aug. 8, 2002) should read http://www.mritutor.org/mritutor/contrast.html On page 3, under Other Publications:

Stephens, J , "Peitier CPU Cooling," http://www.pemech.com/show/processors/140/ (Aug. 13, 2002) should read --Peltier--

Signed and Sealed this

Twenty-first Day of August, 2007

JON W. DUDAS
*Director of the United States Patent and Trademark Office*